United States Patent [19]

Mitsuda et al.

[11] Patent Number: 5,767,295
[45] Date of Patent: Jun. 16, 1998

[54] PROCESS FOR PRODUCING 2-SUBSTITUTED OPTICALLY ACTIVE 2,3-DIHYDRO-4H-PYRAN-4-ONE

[75] Inventors: Masura Mitsuda, Takasago; Junzo Hasegawa, Akashi, both of Japan

[73] Assignee: Kaneka Corporation, Osaka, Japan

[21] Appl. No.: 676,973

[22] Filed: Jul. 8, 1996

[30] Foreign Application Priority Data

Jul. 10, 1995 [JP] Japan .................................. 7-198030
Nov. 22, 1995 [JP] Japan .................................. 7-328314

[51] Int. Cl.$^6$ .................... C07D 315/00; C07F 7/00; B01J 31/00
[52] U.S. Cl. .................... 549/425; 502/150; 549/427; 556/54
[58] Field of Search ................. 556/54; 502/150; 549/425, 427

[56] References Cited

FOREIGN PATENT DOCUMENTS 2 224 735   2/1989   United Kingdom .

OTHER PUBLICATIONS

Keck et al., Journal of Organic Chemistry, vol. 60, No. 19, pp. 5998–5999, Sep. 22, 1995.
Chemical Abstracts 124:55733 (1996).
Chemical Abstracts 122:9813 (1995).
Chemical Abstracts 108:37584 (1988).
Chemical Abstracts 99:5480 (1983).
Corey et al., Enantioselective Mukaiyama–Aldol and Aldol–Dihydropyrone Annulation Reactions Catalyzed by a Tryptophan Derived Oxazaborolidine, Tetrahedron Letters, vol. 33, 1992, pp. 6907–6910.
Keck et al., Pronounced Solvent and Concentration Effects in an Enantioselective Mukaiyama Aldol Condensation Using BINOL–Titanium(IV) Catalysts, J. Am. Chem. Soc., vol. 117, 1995, pp. 2363–2364.
Matsukawa et al., Highly Enantioselective Catalysis of the Mukaiyama Aldol Reaction by BINOL–Ti Perfluorophenoxide and Enoxysilacyclobutane, Tetrahedron; Asymmetry, vol. 6, No. 10, 1995, pp. 2571–2574.

*Primary Examiner*—Porfirio Nazario-Gonzalez
*Attorney, Agent, or Firm*—Pollock, Vande Sande & Priddy

[57] ABSTRACT

The invention provides an efficient process for producing a 2-substituted optically active 2,3-dihydro-4H-pyran-4-one comprising subjecting an aldehyde, which is not bulky and cannot be expected an electronic interaction with a catalyst, such as acetaldehyde, and a Danishefsky diene to a highly enantio-selective asymmetric hetero Diels-Alder reaction in the presence of an asymmetric catalyst readily obtainable from inexpensive starting materials.

17 Claims, No Drawings

PROCESS FOR PRODUCING 2-SUBSTITUTED OPTICALLY ACTIVE 2,3-DIHYDRO-4H-PYRAN-4-ONE

FIELD OF THE INVENTION

The present invention relates to an efficient process for producing optically active intermediates useful for the production of natural type or non-natural type saccharides [S. Danishefsky and M. P. DeNinno; Angew. Chem. Int. Ed. 26, 15, 1987] or for the synthesis of other useful substances such as therapeutic agents for leukotriene-mediated diseases (WO 94/17054).

BACKGROUND OF THE INVENTION

The well-known process for producing an optically active 2,3-dihydro-4H-pyran-4-one having substituent at 2 position (hereinafter referred to as a 2-substituted optically active 2,3-dihydro-4H-pyran-4-one) which is of value as an intermediate for the production of medicinal substances comprises subjecting an aldehyde and an 4-alkoxy-2-trialkylsiloxy-1,3-butadiene (hereinafter referred to as Danishefsky diene) to asymmetric hetero Diels-Alder reaction in the presence of asymmetric catalysts and treating the reaction product with trifluoroacetic acid [① Maruoka et al.: J. Am. Chem. Soc., 110, 310, 1988; ② E. J. Corey: Tetrahedron Lett., 33, 6907, 1992; ③ Motoyama and Mikami: J. Chem. Soc. Chem. Commun., 1563, 1994; ④ Gao et al., Tetrahedron, 50, 979, 1994; ⑤ Sugimoto et al.: The synopsis of the 69th Spring Congress of The Chemical Society of Japan, II-3H525, 1995); and ⑥ M. Bedmarski and S. Danishefsky: J. Am. Chem. Soc., 108, 7060, 1986].

The conventional asymmetric hetero Diels-Alder reaction in the presence of asymmetric catalysts is high in enantioselectivity when the starting aldehyde is sufficiently bulky or when the starting aldehyde shows an interaction of π-electrons with the catalyst. Thus, each of the starting aldehydes used in the above processes ① through ⑤ is either aldehyde having an aromatic ring, such as benzaldehyde, or aldehyde having a bulky substituent group.

However, when a simple saturated aliphatic aldehyde which is not bulky and hence cannot be expected an electronic interaction with the catalyst, such as acetaldehyde, is employed, the stereoselectivity of the reactions is inadequate.

The process ⑥ mentioned above comprises subjecting acetaldehyde and an optically active Danishefsky diene to asymmetric hetero Diels-Alder reaction. However, this optically active Danishefsky diene is expensive and not readily available and the stereoselectively that can be obtained in using thereof is no more than about 70%.

Furthermore, the asymmetric catalysts used in the above known processes are obtainable only after a long series of synthetic steps using starting materials which are not readily available and are, therefore, unsuited for industrial exploitation.

SUMMARY OF THE INVENTION

In view of the above state of the art, the present invention has for its object to provide an efficient process for producing a 2-substituted optically active 2,3-dihydro-4H-pyran-4-one which comprises subjecting an aldehyde, which is not bulky and cannot be expected an electronic interaction with a catalyst, such as acetaldehyde, to a highly enantioselective asymmetric hetero Diels-Alder reaction with a Danishefsky diene in the presence of an asymmetric catalyst readily obtainable from inexpensive starting materials.

The gist of the present invention is a process for producing a 2-substituted optically active 2,3-dihydro-4H-pyran-4-one of the following general formula

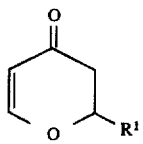

(3)

(wherein $R^1$ represents a substituted or unsubstituted alkyl group having 1 to 15 carbon atoms, a substituted or unsubstituted alkenyl group having 2 to 15 carbon atoms, a substituted or unsubstituted alkinyl group having 2 to 15 carbon atoms, or a substituted or unsubstituted aryl group having 6 to 14 carbon atoms) comprising subjecting an aldehyde of the following general formula (1):

$$R^1CHO \quad (1)$$

(wherein $R^1$ has the same meaning as defined above) and a butadiene derivative of the following general formula (2):

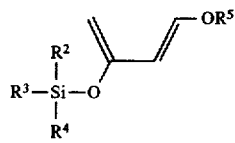

(2)

(wherein $R^2$, $R^3$, and $R^4$ independently represent a substituted or unsubstituted alkyl group having 1 to 15 carbon atoms or a substituted or unsubstituted aryl group having 6 to 14 carbon atoms; $R^5$ represents a substituted or unsubstituted alkyl group having 1 to 15 carbon atoms or a substituted or unsubstituted aryl group having 6 to 14 carbon atoms) to an asymmetric hetero Diels-Alder reaction in the presence of a Chiral Lewis acid viz. a Lewis acid having chirality and treating the resulting reaction mixture product with a protonic acid.

DETAILED DESCRIPTION

There is no particular limitation on the above-mentioned aldehyde of general formula (1). Thus, said aldehyde includes but is not limited to saturated aliphatic aldehydes, unsaturated aliphatic aldehydes, linear aliphatic aldehydes, branched aliphatic aldehydes and alicyclic aliphatic aldehydes, such as acetaldehyde, propion aldehyde, n-butanal, isobutanal, hexanal, cyclohexyl acetaldehyde, crotonaldehyde; aromatic aldehydes such as benzaldehyde, p-methoxybenzaldehyde, 1-naphthaldehyde, and furfural.

The butadiene derivative of general formula (2) includes but is not limited to 4-methoxy-2-trimethyl siloxybutadiene, 4-ethoxy-b2-trimethylsiloxybutadiene, 4-methoxy-2-t-butyldimethylsiloxybutadiene, and 4-ethoxy-2-triethylsiloxybutadiene. Preferred, among them, is 4-methoxy-2-trimethylsiloxybutadiene.

The butadiene derivative of general formula (2) is a Danishefsky diene and can be prepared by the known reaction process described in J. Am. Chem. Soc., 96, 7807, 1974, that is to say by reacting a ketone derivative of the following general formula (6):

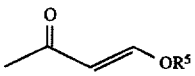

(6)

(wherein $R^3$ has the same meaning as defined hereinbefore) with a silane halide of the following general formula (7):

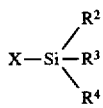
(7)

(wherein X represents a halogen atom; $R^2$, $R^3$, and $R^4$ are the same meaning as defined hereinbefore) in the presence of a base such as triethylamine.

There is no particular limitation on the ketone derivative of general formula (6). Thus, said ketone derivative includes but is not limited to 4-methoxy-3-buten-2-one, 4-ethoxy-3-buten-2-one, 4-propoxy-3-buten-2-one, 4-butoxy-3-buten-2-one, 4-menthyloxy-3-buten-2-one, 4-phenoxy-3-buten-2-one, and 4-p-methoxyphenoxy-3-buten-2-one.

There is no particular limitation on the silane halide of general formula (7) either. Thus, said silane halide includes but is not limited to chlorotrimethylsilane, chlorotriethylsilane, t-butylchlorodimethylsilane, chlorotriphenylsilane, t-butylchlorodiphenylsilane, and iodotrimethylsilane.

The chiral Lewis acid mentioned above is preferably an optically active organotitanium complex. In using such a compound, the asymmetric hetero Diels-Alder reaction can be allowed to proceed with high enantio-selectivity even when an aldehyde which is jot bulky and hence cannot be expected an electronic interaction with the catalyst, such as acetaldehyde, is used as said aldehyde of general formula (1).

The optically active organotitanium complex for use in this reaction is preferably a complex prepared from a titanium tetraalkoxide of the following general formula (5):

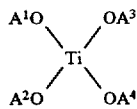
(5)

(wherein $A^1$, $A^2$, $A^3$, and $A^4$ independently represent an alkyl group having 1 to 6 carbon atoms), an optically active 1,1'-bi-2-naphthol, and a substituted or unsubstituted phenol compound having 6 to 14 carbon atoms. The complex thus prepared is hereinafter referred to as being aryl type optically active organotitanium complex.

The aryl type optically active organotitanium complex obtainable from said titanium tetraalkoxide of general formula (5), an approximately equimolar amount of said optically active 1,1'-bi-2-naphthol, and said substituted or unsubstituted phenol compound having 6 to 1 carbon atoms is considered to have the structure represented by the following general formula (4):

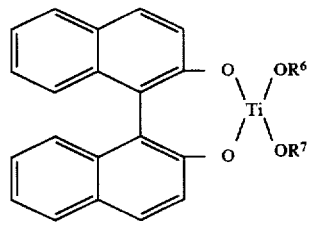
(4)

(wherein $R^6$ represents a substituted or unsubstituted aryl group having 6 to 14 carbon atoms; $R^7$ represents a substituted or unsubstituted aryl group having 6 to 14 carbon atoms or an alkyl group having 1 to 15 carbon atoms; $R^6$ and $R^7$ may be combined to form a ring). The term "approximately equimolar" as used here typically means the range of 0.8 to 1.2 molar equivalents of said optically active 1,1'-bi-2-naphthol with respect to one mole of said titanium tetraalkoxide, but depending on cases the proportion of said optically active 1,1'-bi-2-naphthol may be smaller or larger.

At least one of said $R^6$ and $R^7$ is derived from said substituted or unsubstituted phenol compound having 6 to 14 carbon atoms.

The titanium tetraalkoxide of general formula (5) includes but is not limited to titanium tetramethoxide, titanium tetraethoxide, titanium tetrapropoxide, and titanium tetra-t-butoxide. From the standpoint of availability and ease of handling, titanium tetraiso propoxide is preferred.

There is no particular limitation on the substituted or unsubstituted phenol compound having 1 to 14 carbon atoms. Thus, phenol, 2-methoxyphenol, 2-t-butylphenol, hydroquinone monomethyl ether, chlorophenol, nitrophenol, methylphenol, trifluoromethylphenol, naphthol, o,o'-biphenol, catechol, and 1,1'-bi-2-naphthol can be mentioned, among others. Preferred, among them, are phenol, 2-methoxyphenol and 2-t-butylphenol.

When o,o'-biphenol, catechol, 1,1'-bi-2-naphthol or the like is used as said substituted or unsubstituted phenol compound having 6 to 14 carbon atoms, said $R^6$ and $R^7$ jointly form a ring.

The optically active organotitanium complex can also be prepared from a titanium tetraalkoxide of the following general formula (8):

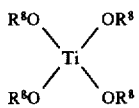
(8)

(wherein $R^8$ represents an alkyl group having 1 to 15 carbon atoms) and an optically active 1,1'-bi-2-naphthol. The complex thus prepared is hereinafter referred to as being alkyl type optically active organotitanium complex. When, in this case, said titanium tetraalkoxide of general formula (8) and said optically active 1,1'-bi-2-naphthol are used in approximately equimolar proportions, the resulting alkyl type optically active organotitanium complex is considered to have the structure represented by the following general formula (9):

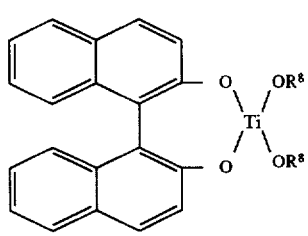
(9)

(wherein $R^8$ represents an alkyl group having 1 to 15 carbon atoms).

The term "approximately equimolar" is used here to mean the range of 0.8 to 1.2 molar equivalents of said optically active 1,1'-bi-2-naphthol with respect to one more of said titaniumtetraalkoxide, and, depending on cases, the proportion of said optically active 1,1'-bi-2-naphthol may be larger or smaller.

When acetaldehyde is used as said aldehyde of general formula (1) and 4-methoxy-2-trimethylsiloxybutadiene as said butadiene derivative of general formula (2), the resulting 2-substituted optically active 2,3-dihydro-4H-pyran-4-one is an optically active 2-methyl-2,3-dihydro-4H-pyran-4-one.

As the 2-substituted optically active 2,3-dihydro-4H-pyran-4-one, (2S)-2-methyl-2,3-dihydro-4H-pyran-4-one can be obtained by conducting an asymmetric hetero Diels- Alder reaction using acetaldehyde as said aldehyde of general formula (1) and 4-methoxy-2-trimethylsiloxybutadiene as said butadiene derivative of general formula (2) in the presence of either an optically active organotitanium complex prepared from titanium tetraisopropoxide, (R)-1,1'-bi-2-naphthol and phenol or an optically active organotitanium complex prepared from titanium tetraisopropoxide and (R)-1,1'-bi-2-naphthol, and then treating the resulting reaction mixture with hydrochloric acid.

The aryl type optically active organotitanium complex mentioned hereinbefore can be prepared typically by the following procedure. First, a titanium tetraalkoxide and 1 to 1.2 molar equivalents of an optically active 1,1'-bi-2-naphthol are mixed and stirred together in a solvent at 0° to 80° C. for 1 to 3 hours. Then, 1 to 3 molar equivalents of a substituted or unsubstituted phenol compound having 6 to 14 carbon atoms is added, and then the resulting mixture is further stirred at 0° to 80° C. for 1 to 3 hours. The solvent is then distilled off under reduced pressure to recover an optically active organotitanium complex as a red-brown substance. This optically active organotitanium complex can be directly subjected to said asymmetric hetero Diels-Alder reaction.

The alkyl type optically active organotitanium complex (9) mentioned hereinbefore can be prepared typically by the following procedure. First, a titanium tetraalkoxide and 1 to 1.2 molar equivalents of an optically active 1,1'-bi-2-naphthol are mixed and stirred in a solvent at 0° to 80° C. for 1 to 3 hours. The solvent is then distilled off under reduced pressure to recover an optically active organotitanium complex as a red-brown substance. This optically active organotitanium complex can be directly subjected to said asymmetric hetero Diels-Alder reaction.

The solvent for use in preparing said optically active organotitanium complex is preferably an aprotic solvent, thus including but not limited to hydrocarbons such as pentane, n-hexane, cyclohexane, benzene, toluene, etc., halogen-containing solvents such as methylene chloride, chloroform, 1,2-dichloroethane, etc., ethers such as diethyl ether, tetrahydrofuran, 1,4-dioxane, etc., acetonitrile and propionitrile.

When 1,1'-bi-2-naphthol, for instance, is used as said substituted or unsubstituted phenol compound having 6 to 14 carbon atoms for the preparation of said aryl type optically active organotitanium complex, 2 to 2.5 molar equivalents of said optically active 1,1'-bi-2-naphthol with respect to one mole of the titanium tetraalkoxide can be included in the starting reaction charge.

In preparing said aryl type optically active organotitanium complex, said substituted or unsubstituted phenol compound having 6 to 14 carbon atoms can be included in the starting reaction charge.

Moreover, in preparing the optically active organotitanium complex, the complex-forming reaction can be hastened by including Molecular sieves (trade name) in the reaction charge.

The chiral Lewis acid which can be used in the present invention also includes the known Lewis acids such as the chiral aluminum complex described, inter alia, by Maruoka et al (J. Am. Chem. Soc., 110, 310, 1988), the chiral boron complex described, inter alia, by E. J. Corey (Tetrahedron Lett., 33, 6907, 1992), the chiral titanium complex described, inter alia, by Motoyama & Mikami (J. Chem. Soc. Chem. Commun., 1563, 1994), and the chiral rare earth metal complex described, inter alia, by M. Bednarski & S. Danishefsky (J. Am. Chem. Soc., 108, 7060, 1986).

The process for producing a 2-substituted optically active 2,3-dihydro-4H-pyran-4-one in accordance with the present invention comprises subjecting said aldehyde of general formula (1) and said butadiene derivative of general formula (2) to an asymmetric hetero Diels-Alder reaction in the presence of said chiral Lewis acid and thereafter treating the resulting reaction mixture with a protonic acid.

The asymmetric hetero Diels-Alder reaction mentioned above can be conducted either in the absence of a solvent or in a reaction solvent.

The reaction solvent mentioned just above is preferably an aprotic solvent and includes but is not limited to hydrocarbons such as pentane, n-hexane, cyclohexane, benzene, toluene, etc., halogen-containing solvents such as methylene chloride, chloroform, 1,2-dichloroethane, etc., acetonitrile, and propionitrile.

The molar ratio of the aldehyde of general formula (1) to the butadiene derivative of general formula (2) may be 1:1 because of the high reaction yield. However, since the reaction time becomes short and the reaction yield becomes to be further improved, the aldehyde of general formula (1) which is inexpensive is preferably used in an excess of 2 to 10 molar equivalents.

The chiral Lewis acid to be used in the present invention is an asymmetric catalyst. There is no particular limitation on the level of addition of the chiral Lewis acid. The preferred level is 0.01 to 0.2 equivalent and, for still better results, 0.05 to 0.1 equivalent with respect to the butadiene derivative of general formula (2).

The amount of the solvent for use in said asymmetric hetero Diels-Alder reaction is preferably 3 to 50 times, by volume/weight, and, for still better results, 5 to 15 times, by volume/weight, with respect to the butadiene derivative of general formula (2) in terms of the charging ratio.

The reaction temperature for said asymmetric hetero Diels-Alder reaction is preferably −100° C. through 100° C. and, for still better results, −30° C. through 50° C.

The asymmetric hetero Diels-Alder reaction can be conducted typically by the following procedure. First, the chiral Lewis acid is dissolved in said reaction solvent and, then, the aldehyde of general formula (1) is added dropwise with stirring. Thereafter, the butadiene derivative of general formula (2) is added dropwise and the mixture is kept under stirring until the asymmetric hetero Diels-Alder reaction has gone to completion. The end point of said asymmetric hetero Diels-Alder reaction can be ascertained by monitoring the exhaustion of the starting compounds by thin-layer chromatography or gas chromatography.

In the practice of the present invention, the order of feeding said chiral Lewis acid, aldehyde of general formula (1), and butadiene derivative of general formula (2) may be changed as desired.

The 2-substituted optically active 2,3-dihydro-4H-pyran-4-one of the present invention can be isolated as follows. After confirming completion of said asymmetric hetero Diels-Alder reaction, said protonic acid is added to the reaction mixture and the mixture is stirred at 0° to 30° C. for 30 to 60 minutes. Then, this mixture is extracted with the common solvent, e.g. diethyl ether, ethyl acetate or methylene chloride, and the organic extract is concentrated to remove the solvent, thus leaving a crude 2-substituted optically active 2,3-dihydro-4H-pyran-4-one. Finally this crude compound is purified by chromatography, recrystallization, distillation, or other procedure.

The protonic acid that can be used includes 1 to 12 normal (1 to 12N) hydrochloric acid, 5 to 98% sulfuric acid, formic acid, acetic acid, trifluoroacetic acid, and so on. Preferred is 1 to 12 normal (1 to 12N) hydrochloric acid.

In accordance with the present invention constituted as above, 2-substituted optically active 2,3-dihydro-4H-pyran- 4-one can be produced starting with an aldehyde and a Danishefsky diene with high efficiency on a commercial scale.

EXAMPLES

The following examples are further illustrative of the present invention but by no means limitative of the scope of the invention.

The following instruments wee used for the various analyses described in the Examples.

Nuclear magnetic resonance spectrometry (NMR): EX-400, Jeol Ltd.

Infrared spectrophotometry (IR): FTIR-8100M, Shimadzu Corporation

High performance liquid chromatography (HPLC): LC-9A, Shimadzu Corporation (UV detector: SPD-6A manufactured by Shimadzu Corporation), chromatopak (C-R6A, Shimadzu Corporation)

Example 1

Synthesis of chiral titanium complex (A)

Under argon gas, 500 mg of Molecular sieves (4A) (trade name), 31.5 mg (0.11 mmol) of (R)-1,1'-bi-2-naphthol, and 30 µl (0.10 mmol) of titanium tetraisopropoxide were stirred in 4 ml of methylene chloride at 20° C. for 1 hour. To the resulting solution was added 19 mg (0.20 mmol) of phenol and the mixture was stirred for 1 hour. This reaction mixture was filtered under reduced pressure to remove insoluble residue and the filtrate was concentrated on an evaporator to remove the solvent to provide chiral titanium complex (A) as a red-brown solid.

This red-brown solid was dissolved in deutero chloroform ($CDCl_2$) and a $^1$H-NMR spectrum was recorded. The appearance of a multiplet at a lower field of 6 to 8 ppm and the disappearance of an isopropyl signal at a higher field indicated that titanium tetraisopropoxide had undergone a ligand exchange reaction with (R)-1,1'-bi-2-naphthol and phenol.

$^2$H-NMR (δ/ppm, $CDCl_3$): 6.8–8.2 (12H, m), 6.70 (4H, d), 6.85 (2H, t), 7.13 (4H, t)

Example 2

The whole amount of chiral titanium complex (A) obtained as a red-brown solid in Example 1 was dissolved in 4.0 ml of the reaction solvent of methylene chloride and one-half or 2.0 ml of the solution (corresponding to 0.05 mmol of the complex) was injected from a syringe into an argon-purged empty reaction flask of 20 ml capacity. After this solution was cooled to 0° C. under argon gas, 55 µl (1.0 mmol) of acetaldehyde and 104 µl (0.5 mmol) of 4-methoxy-2-trimethylsiloxy-1,3-butadiene (synthesized by the process described in J. Am. Chem. Soc., 96, 7807, 1974) are added in order and the mixture was stirred at the same temperature for 2 hours.

To this reaction mixture was added 3 ml of 6N hydrochloric acid, and after 30 minutes of stirring at 20° C., the mixture was extracted with 3 portions of diethyl ether. The ethereal solution of the ether phase was washed with saturated aqueous NaCl solution and dried over anhydrous sodium sulfate and the solvent was then distilled off. The residue was purified by silica gel column chromatography (Wakogel C200 (trade name), hexane/ethyl acetate=7/3) to provide 36 mg of (2S)-2-methyl-2,3-dihydro-4H-pyran-4-one as oil substance (88% e.e., yield 64%).

$^1$H-NMR (δ/ppm, $CDCl_3$): 7.35 (1H, d, J=5.9 Hz), 5.41 (1H, d, J=5.9 Hz), 4.5–4.6 (1H, m), 2.4–2.6 (2H, m), 1.46 (3H, d, J=6.4 Hz).

$^{13}$C-NMR (δ/ppm, $CDCl_3$): 192, 163, 107, 76.0, 43.5, 20.4 IR (v/cm$^{-1}$, film): 1676, 1593, 1289, 1233

The % e.e. (enantiomer excess) was determined by high performance liquid chromatography (HPLC) under the following conditions.

Column: Chiral Cell OB (trade name), manufactured by Daicel Chemical Industries, Ltd.
Eluent: hexane/isopropyl alcohol=9/1
Detection wavelength: 235 nm
Flow rate: 1.0 ml/min.

Example 3

Using toluene as the reaction solvent, the procedure of Example 2 was otherwise repeated to provide 45 mg of (2S)-2-methyl-2,3-dihydro-4H-pyran-4-one (87% e.e., yield 80%) as oily substance.

Example 4

Synthesis of chiral titanium complex (B)

Under argon gas, 500 mg of Molecular sieves (4A) (trade name), 60.1 mg (0.21 mmol) of (R)-1,1∝-bi-2-naphthol, and 30 µl (0.10 mmol) of titanium tetraisopropoxide were stirred in 4 ml of methylene chloride at 20° C. for 1 hour. This solution was then filtered under reduced pressure to remove insoluble residue and the filtrate was concentrated on an evaporator to remove the solvent, whereupon chiral titanium complex (B) was obtained as a red-brown solid.

Example 5

The whole amount of chiral titanium complex (B) obtained as a red-brown solid in Example 4 was dissolved in 4.0 ml of methylene chloride as a reaction solvent and on-half or 2.0 ml of the solution (corresponding to 0.05 mmol of the complex) was injected from a syringe into an argon-purged empty reaction flask of 20 ml capacity. After this solution was cooled to 0° C. under argon gas, 55 µl (1.0 mmol) of acetaldehyde and 104 µl (0.5 mmol) of 4-methoxy-2-trimethylsiloxy-1,3-butadiene were added in that order and the mixture was stirred at the same temperature for 2 hours.

To this reaction mixture was added 3 ml of 6N hydrochloric acid, and after 30 minutes of stirring at 20° C., the mixture was extracted with 3 portions of diethyl ether. The ethereal solution of the ether phase was washed with saturated aqueous NaCl solution and dried over anhydrous sodium sulfate and the solvent was distilled off.

The residue was purified by silica gel column chromatography (Wakogel C200 (trade name), hexane/ethyl acetate=7/3) to provide 19 mg of (2S)-2-methyl-2,3-dihydro-4H-pyran-4-one (86% e.e., yield 34%) as oily substance.

Example 6

Synthesis of chiral titanium complex (C)

Under argon gas, 500 mg of Molecular sieves (4A) (trade name), 31.5 mg (0.11 mmol) of (R)-1,1'-bi-2-naphthol, and 30 µl (0.10 mmol) of titanium tetraisopropoxide were stirred in 4 ml of methylene chloride at 20° C., for 2 hour. To the resulting solution was added 19 mg (0.10 mmol) of o,o'-biphenol and the mixture was stirred for 1 hour. This solution was then filtered under reduced pressure to remove insoluble residue and the filtrate was concentrated on an evaporator to remove the solvent, whereupon chiral titanium complex (C) was obtained as a red-brown solid.

Example 7

The whole amount of chiral titanium complex (C) obtained as a red-brown solid in Example 6 was dissolved in 4.0 ml of methylene chloride as a reaction solvent and con-half or 2.0 ml of the solution (corresponding to 0.05 mmol of the complex) was injected from a syringe into an argon-purged empty reaction flask of 20 ml of capacity. After this solution was cooled to 0° C. under argon gas, 55 μl (1.0 mmol) of acetaldehyde and 104 μl (0.5 mmol) of 4-methoxy-2-trimethylsiloxy-1,3-butadiene were added in that order and the mixture was stirred at the same temperature for 4 hours.

To this reaction mixture was added 3 ml of 6N hydrochloric acid, and after 30 minutes of stirring at 20° C., the mixture was extracted with 3 portions of diethyl ether. The ethereal solution of the ether phase was washed with saturated aqueous NaCl solution and dried over anhydrous sodium sulfate and the solvent was distilled off.

The residue was purified by silica gel column chromatography (Wakogel C200 (trade name), hexane/ethyl acetate=7/3) to provide 24 mg of (2S)-2-methyl-2,3-dihydro-4H-pyran-4-one (61% e.e. yield 43%) as oily substance.

Example 8

Synthesis of chiral titanium complex (D)

Under argon gas, 500 mg of Molecular sieves (4A) (trade name), 31.5 mg (0.11 mmol) of (S)-1,1'-bi-2-naphthol, and 30 μl (0.10 mmol) of titanium tetraisopropoxide were stirred in 4 ml of methylene chloride at 20° C. for 1 hour. To the resulting solution was added 19 mg (0.20 mmol) of phenol and the mixture was stirred for 1 hour. This solution was then filtered under reduced pressure to remove insoluble residue and the filtrate was concentrated on an evaporator to remove the solvent, whereupon chiral titanium complex (D) was obtained as a red-brown solid.

Example 9

The whole amount of chiral titanium complex (D) obtained as a red-brown solid in Example 8 was dissolved in 4.0 ml of reaction solvent of methylene chloride and one-half or 2.0 ml of the solution (corresponding to 0.05 mmol of the complex) was injected from a syringe into an argon-purged empty reaction flask of 20 ml capacity. After this solution was heated to 30° C. under argon gas, 55 μl (1.0 mmol) of acetaldehyde and 104 μl (0.5 mmol) of 4-methoxy-2-trimethylsiloxy-1,3-butadiene were added in that order and the mixture was stirred at the same temperature for 1.5 hours.

To this reaction mixture was added 3 ml of 6N hydrochloric acid, and after 30 minutes of stirred at 20° C., the mixture was extracted with 3 portions of diethyl ether. The ethereal solution of the ether phase was washed with saturated aqueous NaCl solution and dried over anhydrous sodium sulfate and the solvent was distilled off. The residue was purified by silica gel column chromatography (Wakogel C200 (trade name), hexane/ethyl acetate=7/3) to provide 34 mg of (2R)-2-methyl-2,3-dihydro-4H-pyran-4-one (91% e.e., yield 61%) as oily substance.

Example 10

Synthesis of chiral titanium complex (E)

Under argon gas 500 mg of Molecular sieves (4A) (trade name), 31.5 mg (0.11 mmol) of (R)-1,1'-bi-2-naphthol, and 30 μl (0.10 mmol) of titanium tetraisopropoxide were stirred in 4 ml of methylene chloride at 20° C. for 1 hour. This solution was then filtered under reduced pressure to remove insoluble residue and the filtrate was concentrated on an evaporator to remove the solvent, whereupon chiral titanium complex (E) was obtained as a red-brown solid.

$^1$H-NMR (δ/ppm, CDCl$_2$): 1.03 (12H, bd), 3.82 (2H, m), 6.5–8.2 (12H, m)

Example 11

The whole amount of chiral titanium complex (E) obtained as a red-brown solid in Example 10 was dissolved in 4.0 ml of reaction solvent of methylene chloride and one-half or 2.0 ml of the solution (corresponding to 0.05 mmol of the complex) was injected from a syringe into an argon-purged empty reaction flask of 20 ml capacity. After this solution was cooled to 0° C. under argon gas, 55 μl (1.0 mmol) of acetaldehyde and 104 μl (0.5 mmol) of 4-methoxy-2-trimethylsiloxy-1,3-butadiene were added in that order and the mixture was stirred at the same temperature for 2 hours.

To this reaction mixture was added 3 ml of 6 N hydrochloric acid, and after 30 minutes of stirring at 20 ° C., the mixture was extracted with 3 portions of diethyl ether. The ethereal solution of the ether phase was washed with saturated aqueous NaCl solution and dried over anhydrous sodium sulfate and the solvent was distilled off.

The residue was purified by silica gel column chromatography (Wakogel C200 (trade name), hexane/ethyl acetate=7/3) to provide 24 mg of (2S)-2-methyl-2,3-dihydro-4H-pyran-4-one (89% e.e., yield 43%) as oily substance.

Example 12

Synthesis of chiral titanium complex (F)

Under argon gas, 500 mg of Molecular sieves (4A) (trade name), 31.5 mg (0.11 mmol) of (R)-1,1'-bi-2-naphthol, and 30 μl (0.10 mmol) of titanium tetraisopropoxide were stirred in 4 ml of methylene chloride at 20° C. for 1 hour. To the resulting solution was added 24.8 mg (0.20 mmol) of guaiacol (2-methoxyphenol) as phenol compound and the mixture was stirred for 1 hour. This solution was then filtered under reduced pressure to remove insoluble residue and the filtrate was concentrated on an evaporator to remove the solvent, whereupon chiral titanium complex (F) was obtained as a red-brown solid.

Examples 13 to 21

Synthesis of chiral titanium complexes (G), (H), (I), (J), (K), (L), (M), (N), and (O)

Using the phenol compounds listed in Table 1, respectively, the procedure of Example 12 was otherwise repeated to provide chiral titanium complexes (G), (B), (I), (J), (K), (L), (M), (N), and (O) as brown solids.

TABLE 1

| Example | Phenol compound | Chiral titanium complex |
|---|---|---|
| 13 | 2-t-Butylphenol | (G) |
| 14 | 4-t-Butylphenol | (H) |
| 15 | 2,4,6-Trichlorophenol | (I) |
| 16 | 2,4,6-Trimethylphenol | (J) |
| 17 | Hydroquinone methyl ether | (K) |

TABLE 1-continued

| Example | Phenol compound | Chiral titanium complex |
|---|---|---|
| 18 | 4-Nitrophenol | (L) |
| 19 | 1-Napthol | (M) |
| 20 | Cresol | (N) |
| 21 | 2-Chorophenol | (O) |

Example 22

The whole amount of chiral titanium complex (F) obtained as a red-brown solid in Example 12 was dissolved in 4.0 ml of Methylene chloride and on-half or 2.0 ml of the solution (corresponding to 0.05 mmol of the complex) was injected from a syringe into an argon-purged empty reaction flask of 20 ml capacity. After this solution was cooled to 0° C., under argon gas, 55 µl (1.0 mmol) of acetaldehyde and 104 µl (0.5 mmol) of 4-methoxy-2-trimethylsiloxy-1,3-butadiene were added in that order and the mixture was stirred at the same temperature for 2 hours.

To this reaction mixture was added 3 ml of 6N hydrochloric acid, and after 30 minutes of stirring at 20° C., the mixture was extracted with 3 portions of diethyl ether. The ethereal solution of the ether phase was washed with saturated aqueous NaCl solution and dried over anhydrous sodium sulfate and the solvent was distilled off.

The residue was purified by silica gel column chromatography (Wakogel C200 (trade name), hexane/ethyl acetate=7/3) to provide 30 mg of (2S)-2-methyl-2,3-dihydro-4H-pyran-4-one (93% e.e., yield 54%) as oily substance.

Example 23 to 31

Using the chiral titanium complexes (G), (H), (I), (J), (K), (L), (M), (N), and (O) synthesized in Examples 13 to 23, respectively, the procedure of Example 22 was otherwise repeated to provide (2S)-2-methyl-2,3-dihydro-4H-pyran-4-one. The data are presented in Table 2.

TABLE 2

| Example | Chiral titanium complex | % yield | % e.e. |
|---|---|---|---|
| 23 | (G) | 45 | 93 |
| 24 | (H) | 25 | 80 |
| 25 | (I) | 30 | 86 |
| 26 | (J) | 41 | 78 |
| 27 | (K) | 54 | 87 |
| 28 | (L) | 12 | 63 |
| 29 | (M) | 37 | 82 |
| 30 | (N) | 34 | 81 |
| 31 | (O) | 54 | 87 |

Example 32

The whole amount of chiral titanium complex (A) obtained as a red-brown solid in Example 1 was dissolved in 4.0 ml of reaction solvent of methylene chloride and one-half or 2.0 ml of the solution (corresponding to 0.05 mmol of the complex) was injected from a syringe into an argon-purged empty reaction flask of 20 ml capacity. After this solution was cooled to 0° C. under argon gas, 90 µl (1.0 mmol) of n-butanal and 104 µl (0.5 mmol) of 4-methoxy-2-trimethylsiloxy-1,3-butadiene were added in that order an the mixture was stirred at the same temperature for 3 hours.

To this reaction mixture was added 3 ml of 6N hydrochloric acid, and after 30 minutes of stirring at 20° C., the mixture was extracted with 3 portions of diethyl ether. The ethereal solution of the ether phase was washed with saturated aqueous NaCl solution and dried over anhydrous sodium sulfate and the solvent was distilled off.

The residue was purified by silica gel column chromatography to provide 27 mg of (2S)-2-n-propyl-2,3-dihydro-4H-pyran-4-one (94% e.e., yield 39%) as oily substance.

The % e.e. was determined by HPLC as in Example 2.
$^1$H-NMR (δ/ppm, CDCl$_3$): 7.36 (1H, d, J=5.9 Hz), 5.40 (1H, d, J=5.9 Hz), 4.3–4.5 (1H, m), 2.52 (1H, dd, J=15.5, 13.2 Hz), 2.43 (1H, dd, J=16.6, 3.9 Hz), 1.7–1.9 (1H, m), 1.4–1.7 (3H, m), 0.97 (3H, t, J=7.3 Hz)

$^{13}$C-NMR (δ/ppm, CDCl$_3$): 193, 163, 107, 79.3, 41.8, 36.5, 18.0, 13.8

Example 33

The whole amount of chiral titanium complex (A) obtained as a red-brown solid in Example 11 was dissolved in 4.0 ml of reaction solvent of methylene chloride and one-half or 2.0 ml of the solution (corresponding to 0.05 mmol of the complex) was injected from a syringe into an argon-purged empty reaction flask of 20 ml capacity. After this solution was cooled to 20° C. under argon gas, 91 µl (1.0 mmol) of i-butanal and 104 µl (0.5 mmol) of 4-methoxy-2-trimethylsiloxy-1,3-butadiene were added in that order and the mixture was stirred at the same temperature for 3 hours.

To this reaction mixture was added 3 ml of 6N hydrochloric acid, and after 30 minutes of stirring at 20° C., the mixture was extracted with 3 portions of diethyl ether. The ethereal solution of the ether phase was washed with saturated aqueous NaCl solution and dried over anhydrous sodium sulfate and the solvent was distilled off.

The residue was purified by silica gel column chromatography to provide 8 mg of (2S)-2-i-propyl-2,3-dihydro-4H-pyran-4-one (86% e.e., yield 11%) as oily substance.

The % e.e. was determined by HPLC as in Example 2.
$^3$H-NMR (δ/ppm, CDCl$_3$): 7.39 (1H, d, J=5.9 Hz), 5.40 (1H, d, J=5.9 Hz), 4.1–4.2 (1H, m), 2.53 (1H, dd, J=16.6, 14.7 Hz), 2.39 (1H, dd, J=16.6, 3.4 Hz), 1.95–2.02 (1H, m), 1.02 (3H, d, J=6.8 Hz), 1.00 (3H, D, J=6.8 Hz)

$^{15}$C-NMR (δ/ppm, CDCl$_3$): 193, 164, 107, 84.1, 38.9, 31.8, 17.8, 17.6

Example 34

The whole amount of chiral titanium complex (A) obtained as a red-brown solid in Example 1 was dissolved in 4.0 ml of methylene chloride and one-half or 2.0 ml of the solution (corresponding to 0.05 mmol of the complex) was injected from a syringe into an argon-purged empty reaction flask of 20 ml capacity. After this solution was cooled to 0° C. under argon gas, 126 µl (1.0 mmol) of trans-cinnamaldehyde and 104 µl (0.5 mmol) of 4-methoxy-2-trimethylsiloxy-1,3-butadiene were added in that order an the mixture was stirred at the same temperature for 3 hours.

To this reaction mixture was added 3 ml of 6N hydrochloric acid, and after 30 minutes of stirring at 20° C., the mixture was extracted with 3 portions of diethyl ether. The ethereal solution of the ether phase was washed with saturated aqueous NaCl solution and dried over anhydrous sodium sulfate and the solvent was distilled off.

The residue was purified by silica gel column chromatography to provide 22 mg of (2S)-2-(2-phenylvinyl)-2,3-dihydro-4H-pyran-4-one (44% e.e., yield 22%) as oily substance.

The % e.e. was determined by HPLC as in Example 2.

Example 35

The whole amount of chiral titanium complex (A) obtained as a red-brown solid in Example 1 was dissolved in 4.0 ml of methylene chloride and one-half or 2.0 ml of the solution (corresponding to 0.05 mmol of the complex) was injected from a syringe into an argon-purged empty reaction flask of 20 ml capacity. After this solution was cooled to 0° C. under argon gas, 156 μl (1.0 mmol) of n-octanal and 104 μl (0.5 mmol) of 4-methoxy-2-trimethylsiloxy-1,3-butadiene were added in that order and the mixture was stirred at the same temperature for 3 hours.

To this reaction mixture was added 3 ml of 6N hydrochloric acid, and after 30 minutes of stirring at 20° C., the mixture was extracted with 3 portions of diethyl ether. The ethereal solution of the ether phase was washed with saturated aqueous NaCl solution and dried over anhydrous sodium sulfate and the solvent was distilled off.

The residue was purified by silica gel column chromatography to provide 39 mg of (2S)-2-n-heptyl-2,3-dihydro-4H-pyran-4-one (88% e.e., yield 40%) as oily substance.

The % e.e. was determined by HPLC as in Example 2.

$^1$H-NMR (δ/ppm, CDCl$_2$): 7.39 (1H, d, J=5.9 Hz), 5.41 (1H, d, J=5.9 Hz), 4.35–4.45 (1H, m), 2.52 (1H, dd, J=15.5, 13.2 Hz), 2.43 (1H, dd, J=16.6, 3.9 Hz), 1.2–1.9 (12H, m), 0.89 (3H, d, J=6.8 Hz)

$^{15}$C-NMR (δ/ppm, CDCl$_3$): 193, 164, 107, 79.6, 41.8, 34.4, 31.7, 29.3, 29.1, 24.8, 22.6, 14.1

We claim:

1. A process for producing a 2-substituted optically active 2,3-dihydro-4H-pyran-4-one of general formula (3):

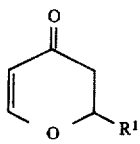

(3)

(wherein R$^1$ represents a substituted or unsubstituted alkyl group having 1 to 15 carbon atoms, a substituted or unsubstituted alkenyl group having 2 to 15 carbon atoms, a substituted or unsubstituted alkinyl group having 2 to 15 carbon atoms, or a substituted or unsubstituted aryl group having 6 to 14 carbon atoms) comprising subjecting an aldehyde of general formula (1):

 (1)

(wherein R$^1$ has the same meaning as defined above) and a butadiene derivative of general formula (2):

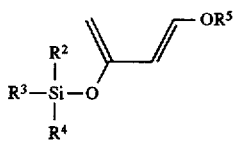

(2)

(wherein R$^2$, R$^3$, and R$^4$ independently represent a substituted or unsubstituted alkyl group having 1 to 15 carbon atoms or a substituted or unsubstituted aryl group having 6 to 14 carbon atoms; R$^5$ represents a substituted or unsubstituted alkyl group having 1 to 15 carbon atoms or a substituted or unsubstituted aryl group having 6 to 14 carbon atoms) to an asymmetric hetero Diels-Alder reaction in the presence of a Lewis acid having chirality and treating the resulting reaction mixture with a protonic acid.

2. A process according to claim 1 wherein said aldehyde is acetaldehyde and said butadiene derivative is 4-methoxy-2-trimethyl siloxybutadiene, and said 2-substituted optically active 2,3-dihydro-4H-pyran-4-one is an optically active 2-methyl-2,3-dihydro-4H-pyran-4one.

3. The process for producing a 2-substituted optically active 2,3-dihydro-4H-pyran-4-one according to claim 1 wherein said Lewis acid having chirality is an optically active organotitanium complex prepared from a titanium tetraalkoxide of general formula (5):

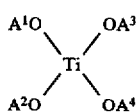

(5)

(wherein A$^1$, A$^2$, A$^3$, and A$^4$ independently represent an alkyl group having 1 to 6 carbon atoms), an optically active 1,1'-bi-2-naphthol, and a substituted or unsubstituted phenol compound having 6 to 14 carbon atoms.

4. The process for producing a 2-substituted optically active 2,3-dihydro-4H-pyran-4-one according to claim 3 wherein said substituted or unsubstituted phenol compound having 6 to 14 carbon atoms is at least one species selected from the group consisting of phenol, 2-methoxyphenol, and 2-t-butylphenol.

5. The process for producing a 2-substituted optically active 2,3-dihydro-4H-pyran-4-one according to claim 3 wherein said titanium tetraalkoxide is titanium tetraisopropoxide.

6. The process for producing a 2-substituted optically active 2,3-dihydro-4H-pyran-4-one according to claim 3 wherein said Lewis acid having chirality is an optically active organotitanium complex of general formula (4):

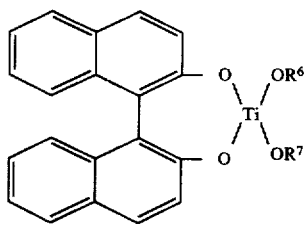

(4)

(wherein R$^6$ represents a substituted or unsubstituted aryl group having 6 to 14 carbon atoms; R$^7$ represents a substituted or unsubstituted aryl group having 6 to 14 carbon atoms or a alkyl group having 1 to 15 carbon atoms; R$^6$ and R$^7$ may be combined to form a ring).

7. The process for producing a 2-substituted optically active 2,3-dihydro-4H-pyran-4-one according to claim 1 wherein said Lewis acid having chirality is an optically active organotitanium complex prepared from a titanium tetraalkoxide of general formula (8):

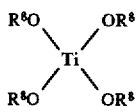

(8)

(wherein R$^8$ represents an alkyl group having 1 to 15 carbon atoms) and an optically active 1,1'-bi-2-naphthol.

8. The process for producing a 2-substituted optically active 2,3-dihydro-4H-pyran-4-one according to claim 7 wherein said Lewis acid having chirality is an optically active organotitanium complex of general formula (9):

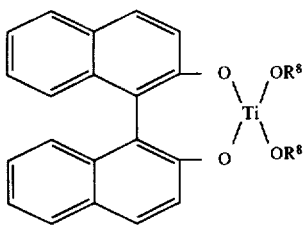

(wherein $R^9$ represents an alkyl group having 1 to 15 carbon atoms).

9. The process for producing a 2-substituted optically active 2,3-dihydro-4H-pyran-4-one according to claim 1 wherein said protonic acid is hydrochloric acid.

10. A process for producing (2S)-2-methyl-2,3-dihydro-4H-pyran-4-one comprising subjecting acetaldehyde and 4-methoxy-2-trimethylsiloxybutadiene to an asymmetric hetero Diels-Alder reaction in the presence of an optically active organotitanium complex prepared from at least one phenol compound selected from the group consisting of phenol, 2-methoxyphenol and 2-t-butylphenol; titanium tetraisopropoxide; and (R)-1,1'-bi-2-naphthol, and thereafter treating the resulting reaction mixture with hydrochloric acid.

11. An optically active organotitanium complex comprising a reaction product prepared from a titanium tetraalkoxide of general formula (5):

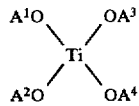
(5)

(wherein $A^1$, $A^2$, $A^3$, and $A^4$ independently represent an alkyl group having 1 to 6 carbon atoms), an optically active 1,1'-bi-2-naphthol, and a substituted or unsubstituted phenol compound having 6 to 14 carbon atoms.

12. An optically active organotitanium complex of general formula (4):

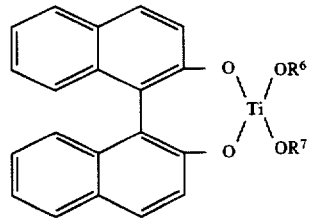
(4)

(wherein $R^6$ represents a substituted or unsubstituted aryl group having 6 to 14 carbon atoms; $R^7$ represents a substituted or unsubstituted aryl group having 6 to 14 carbon atoms or an alkyl group having 1 to 15 carbon atoms; $R^6$ and $R^7$ may be combined to form a ring).

13. An optically active organotitanium complex comprising a reaction product prepared from at least one phenol compound selected from the group consisting of phenol, 2-methoxyphenol and 2-t-butylphenol; titanium tetraisopropoxide; and an optically active 1,1'-bi-2-naphthol.

14. An optically active organotitanium complex comprising a reaction product prepared from a titanium tetraalkoxide of general formula (8):

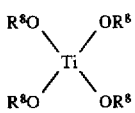
(8)

(wherein $R^8$ represents an alkyl group having 1 to 15 carbon atoms) and an optically active 1,1'-bi-2-naphthol.

15. An optically active organotitanium complex of general formula (9)

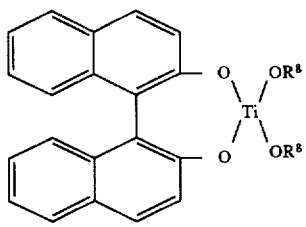
(9)

(wherein $R^8$ represents an alkyl group having 1 to 15 carbon atoms).

16. The optically active organotitanium complex according to claim 14 wherein $R^8$ represents isopropyl.

17. The optically active organotitanium complex according to claim 15 wherein $R^8$ represents isopropyl.

* * * * *